United States Patent [19]

Buirley et al.

[11] 4,433,637

[45] * Feb. 28, 1984

[54] MICROENCAPSULATED CHOLESTERIC LIQUID CRYSTAL TEMPERATURE MEASURING DEVICE FOR DETERMINING THE TEMPERATURE OF NON-PLANAR OR PLANAR SURFACES

[75] Inventors: William L. Buirley, Dayton; Donald E. Koopman, Miami Township, Montgomery County; David B. McQuain, Dayton; William H. Reeves, Englewood, all of Ohio

[73] Assignee: Vectra International Corporation, Miamisburg, Ohio

[*] Notice: The portion of the term of this patent subsequent to Nov. 17, 1998 has been disclaimed.

[21] Appl. No.: 272,194

[22] Filed: Jun. 10, 1981

Related U.S. Application Data

[63] Continuation-in-part of Ser. No. 45,276, Jun. 4, 1979, Pat. No. 4,301,054.

[51] Int. Cl.$^3$ .................. G01D 21/00; G01K 11/12
[52] U.S. Cl. .................. 116/207; 128/736; 252/299.7; 252/962; 350/351; 374/137; 374/162; 428/1
[58] Field of Search ............ 252/316, 299.7, 962; 428/1; 128/736; 374/137, 162; 350/334, 344, 351; 116/207

[56] References Cited

U.S. PATENT DOCUMENTS

| Re. 30,446 | 12/1980 | Myers et al. . | |
|---|---|---|---|
| 3,409,404 | 11/1968 | Fergason | 252/299 X |
| 3,578,844 | 5/1971 | Churchill et al. | 252/316 X |
| 3,585,381 | 6/1971 | Hodson et al. | 252/299 X |
| 3,661,142 | 5/1972 | Flam | 73/356 |
| 3,796,884 | 3/1974 | Tricoire . | |
| 4,100,103 | 7/1978 | Foris et al. | 252/316 |
| 4,135,497 | 1/1979 | Meyers et al. . | |
| 4,185,904 | 1/1980 | Eddy . | |
| 4,202,608 | 5/1980 | Kaufmann | 350/334 X |
| 4,301,054 | 11/1981 | Buirley et al. | 252/316 X |
| 4,327,742 | 5/1982 | Meyers et al. | 128/736 |

FOREIGN PATENT DOCUMENTS

| 2536773 | 2/1977 | Fed. Rep. of Germany | 73/356 |
|---|---|---|---|
| 2110505 | 6/1972 | France | 73/356 |
| 2321395 | 3/1977 | France | 73/356 |
| 487923 | 1/1976 | U.S.S.R. | 252/299 |

OTHER PUBLICATIONS

Gautherie et al.: "Thermographie Cholesterique", Pathologie Biologie, Sep. 1974, pp. 554–564.

*Primary Examiner*—Richard D. Lovering
*Attorney, Agent, or Firm*—Jacox & Meckstroth

[57] ABSTRACT

A temperature measuring device engageable with a surface of any contour to determine the individual temperature of each of the several portions of the surface by providing a thermal map. The map is observable and may be photographed if a record thereof is desired.

The temperature measuring device has a portion engageable with the surface and conformable to the surface. The portion which engages the surface includes a coating of cholesteric material, such as microencapsulated liquid crystal material which is temperature-sensitive and light-reflecting. The device also includes a transparent fill material therewithin to transmit the thermal image or map therethrough. Thus, a thermal map or image of the surface is provided. The thermal map is observable and/or recordable through another portion of the device.

17 Claims, 4 Drawing Figures

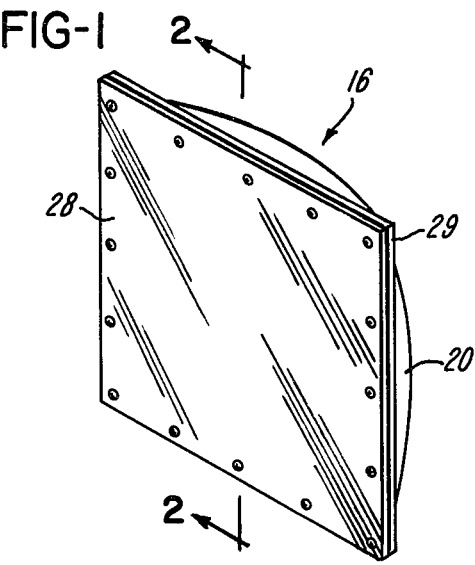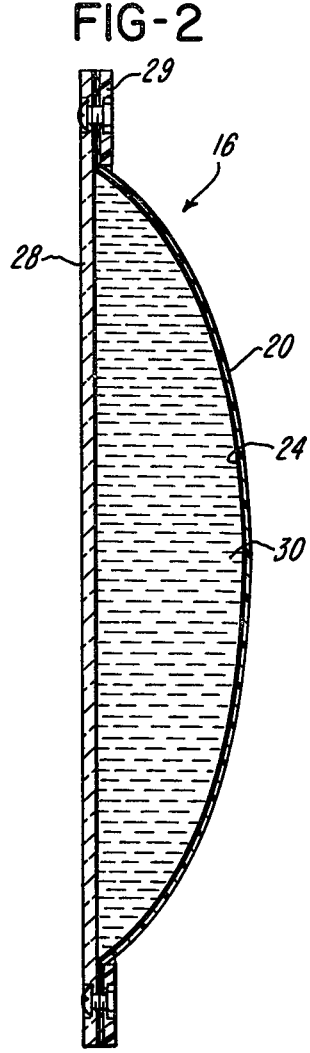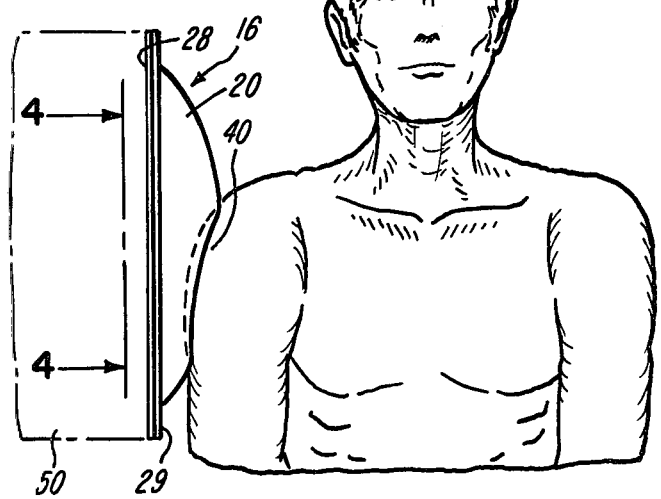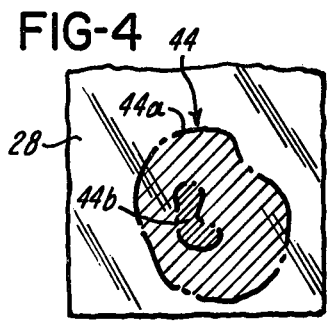

MICROENCAPSULATED CHOLESTERIC LIQUID CRYSTAL TEMPERATURE MEASURING DEVICE FOR DETERMINING THE TEMPERATURE OF NON-PLANAR OR PLANAR SURFACES

This application is a continuation-in-part of application Ser. No. 045,276, filed June 4, 1979 now U.S. Pat. No. 4,301,054.

BACKGROUND OF THE INVENTION

Liquid crystals consisting of mixed cholesteric esters are known to undergo color changes at very specific temperatures in the neighborhood of normal room temperature or body temperature. Consequently, such liquid crystals have been found to be very sensitive indicators of small differences in temperature. This has permitted the liquid crystal materials to be used as extremely accurate temperature indicators and to be used to monitor locations in which temperature differences exist, by providing visual indication of the location of zones of differing heat capacity or differing vascularity in living tissues, for medical or veterinarial purposes, or the location of discontinuities, such as flaws in articles supplied with heat for industrial or constructional purposes.

The practical use of liquid crystals has been somewhat inconvenient in that successful surface contact with contoured surfaces has not been possible with the normally available liquid crystal materials coated onto a substrate, such as a Mylar substrate.

An object of this invention is to provide a device containing liquid crystals, such as microencapsulated liquid crystals, which is capable of providing thermal maps or thermal images of non-planar or planar surfaces. Uses for this invention may be divided into at least two large classes.

1. Thermal maps or thermal images of contoured or planar surfaces of the human body.
2. Thermal maps or thermal images of contoured or planar surfaces of industrial or structural items.

Since liquid crystals have the ability to selectively scatter light and produce color images dependent upon the temperature of their environment, they may be used to project a visual, color picture of the transient temperature anomalies, or minute thermal gradients associated with material discontinuities. Locations of zones or regions of differing temperatures in the human body may be observable in a color picture. As for example, infection can cause inflamation, increased blood flow and heat in an internal organ. That heat may be projected to the surface of the skin and observable in a thermograph. An inflamed appendix or gall bladder infection often creates an area of elevated temperature on the skin. Diseases of the veins and arteries which cause clotting, dilation, or narrowing of the vessels similarly may cause temperature variations in adjacent areas of the skin. These temperature variations may be lower or higher than the temperature of surrounding tissues.

In industrial or structural items discontinuities may, for example, be debonds, cracks, or other defect areas, which sufficiently impede the flow of heat to disturb the normal temperature patterns of a material being tested. The defects then appear as distinct color patterns, as a result of their impaired thermal transmission characteristics.

Until recently, the only thermography available was performed with very expensive equipment and required a controlled temperature environment and a draft free room. The invention herein provides for the first time a low cost, portable instrument for thermographic use in detecting or determining the temperature of a planar or contoured surface.

The preferred thermographic compositions of this invention comprise mixtures of cholesteryl esters as the core material of microcapsules having transparent or translucent walls. Preferably, the microcapsule wall material is polymeric film material such as gelatin urea-formaldehyde, or melamine-formaldehyde polymer material. When the microcapsule wall material is gelatin, the method of encapsulation disclosed in U.S. Pat. No. 2,800,456 is used. For microcapsules having urea-formaldehyde polymer wall material, the encapsulation method of U.S. Pat. No. 4,001,140, particularly, Example 1 thereof, is advantageously used. For microcapsules having melamine-formaldehyde polymer wall material, the encapsulation method of U.S. Pat. No. 4,100,103 is advantageously used.

The thermographic core material of the microcapsules used in the composition of this invention is a mixture of cholesteryl pelargonate, oleyl cholesteryl carbonate, cholesteryl propionate and cholesteryl chloride. The point at which a readily-observable temperature-dependent color change in the composition occurs can be varied by varying the proportion of the four cholesteryl derivatives in the core material mixture. In all cases, the compositions contain major amounts of cholesteryl pelargonate and oleyl cholesteryl carbonate, and minor amounts of cholesteryl propionate and cholesteryl chloride.

The compositions of this invention give a regular series of more-or-less evenly-spaced color changes of gray to red to green to blue over a total range of 3 to 4 centigrade degrees for use in measuring surface temperature of the human body, normal and pathological. Compositions showing gray-red-green-blue color changes in the range of about 27° C. to about 37° C. are useful. A series of compositions can be prepared, varying in one centigrade degree increments (or less if desired) from a 30° C. composition to a 37° C. composition. Particularly useful compositions of this type can be made by the microencapsulation of core materials of the following formulations:

TABLE I

| Middle-Green Temperature | Pelargonate (%) | Oleyl Carbonate (%) | Propionate (%) | Chloride (%) |
|---|---|---|---|---|
| (1) 30° | 66.4 | 21.6 | 5.5 | 6.5 |
| (2) 31° | 66.5 | 22.0 | 4.6 | 6.9 |
| (3) 32° | 68.0 | 20.3 | 4.7 | 7.0 |
| (4) 33° | 70.0 | 18.3 | 4.7 | 7.0 |
| (5) 34° | 71.0 | 17.3 | 4.7 | 7.0 |
| (6) 35° | 72.7 | 15.6 | 4.7 | 7.0 |
| (7) 36° | 73.2 | 15.0 | 5.4 | 6.4 |
| (8) 37° | 73.4 | 14.5 | 5.6 | 6.5 |

A special feature of this core material is directed to compositions comprising preferably about equal parts of two of the microencapsulated core material formulations, chosen with a 3° increment, so as to give over-lapping ranges with a total color transition width of about 7 centigrade degrees. However, satisfactory compositions have been obtained with unequal parts up to a ratio of 70-30, without significant loss of brightness, Thus, one part of microencapsulated core material of the 30° composition, No. 1, mixed with one part of microencapsulated core material of the 33° composition, No. 4, gives a composition showing regular color changes, in response to temperature changes from about 27.5° C. to about 34° C. The partial over-lapping of the two color transition ranges of the 30° C. composition and the 33° C. composition gives rise to seven readily-distinguishable color changes: alpha gray, beta red, beta green, beta blue, gamma red, gamma green and gamma blue. The beta hues are predominantly derived from the lower-range composition, namely the 30° C. composition in this case, and the gamma hues are predominantly derived from the higher-range composition, that is the 33° C. composition in this case. The alpha gray is the gray of the 30° C. composition. The beta hues are the primary hues of the 30° C. composition, shaded by the appearance of the gray and red of the 33° C. composition. The gamma hues are the primary hues of the 33° C., shaded by the blue of the 30° C. composition. The beta hues are readily distinguished from the gamma hues such that the entire color transition range gives seven readily recognized colors in response to temperature variations over about a 7-degree range.

Similarly useful mixtures, exhibiting a 7-degree color transition range, but operating at higher temperatures can be made with equal parts of the following compositions: (from the above formulated table) Nos. (2) and (5), Nos. (3) and (6), Nos. (4) and (7), and Nos. (5) and (8).

For greater sensitivity to small temperature changes, compositions having a narrower color transition range are made. Compositions in this formulation range have a color transition range width of about 2 centigrade degrees for the red to green to blue transition, or about 3 centigrade degrees for the total gray through blue transition. A series of seven compositions can be prepared, varying in one-degree increments (or less, if desired) from about 24° C. to 35° C. as shown in the formulation table set forth.

TABLE II

| Middle-Green Temperature | Pelargonate (%) | Oleyl Carbonate (%) | Propionate (%) | Chloride (%) |
|---|---|---|---|---|
| (9) 24° | 58.6 | 31.7 | 4.1 | 5.6 |
| (10) 26° | 61.1 | 29.6 | 3.7 | 5.6 |
| (11) 28° | 63.0 | 28.4 | 3.0 | 5.6 |
| (12) 29° | 58.5 | 33.9 | 2.4 | 5.2 |
| (13) 30° | 60.7 | 31.5 | 2.4 | 5.4 |
| (14) 31° | 61.2 | 31.5 | 2.5 | 4.8 |
| (15) 32° | 62.2 | 30.7 | 2.1 | 5.0 |
| (16) 33° | 63.5 | 29.2 | 2.2 | 5.1 |
| (17) 34° | 65.3 | 27.2 | 2.6 | 4.9 |
| (18) 35° | 66.3 | 26.2 | 2.6 | 4.9 |

Mixing of equal parts of related formulations, after separate microencapsulation thereof, having over-lapping color transition ranges can be effected to give compositions having a beta red to gamma blue transition width of about 3.5 centigrade degrees, or a width of about 4 centigrade degrees, for all of the alpha gray-gamma blue transitions. From the formulation table set forth above, particularly useful compositions are obtained by mixing formulations Nos. 9 and 10, Nos. 10 and 11, Nos. 11 and 13, Nos. 12 and 14, Nos. 13 and 15, Nos. 14 and 16, Nos. 15 and 17, and Nos. 16 and 18.

The various formulations set out in the table above and variations thereon which the artisan can readily derive from the teachings of this disclosure are useful as visual temperature indicators when applied to a surface such as the human skin. The formulations are advantageously used as the core material in microcapsules, having substantially transparent or translucent polymeric wall material. The microcapsule containing one of the thermographic formulations, either separately or mixed with microcapsules containing a second of the thermographic formulations, are most useful when coated onto a substrate sheet material.

Among the more useful flexible binders for holding the microcapsules on the substrate are polyurethane latexes, such as those sold under the trademarks "A-2701-44" by Hughson Chemical, Erie, PA, "Desmocoll E-471" and "E-723" by Mobay Chemical Corporation, Pittsburg, PA, and "Hooker 2050-L", "2030" and "2060" by Hooker Chemical Corporation, Hicksville, NY. The preferred flexible binder latex is "Desmocoll E-723".

In practice, in a device of this invention, a substrate, preferably a non-transparent film, particularly a polyurethane film containing carbon black is coated with the described microcapsules, each of which contains, as core material, a micro-droplet of a cholesteric formulation, as set out in the table above. It is obvious that any flexible, elastic material which is compatible with the encapsulated cholesteric material and the fill material can be used as the substrate. A microcapsular coating slurry specifically for flexibility and elasticity is prepared by mixing:

121 grams aqueous microcapsule slurry (56.1% solids)
34 grams of 40% polyurethane latex (Desmocoll E-732)
6 grams of distilled water
2 grams of a 1% aqueous solution of alkylaryl polyether alcohol wetting agent, (Triton X-100, Rohm and Haas, Philadelphia, PA).

Throughout this disclosure, percents are percents by weight, and temperature is expressed in degrees centigrade.

BRIEF DESCRIPTION OF THE VIEWS OF THE DRAWINGS

FIG. 1 is a perspective view of a temperature measuring device of this invention.

FIG. 2 is an enlarged sectional view of the temperature measuring device of FIG. 1, taken substantially on line 2—2 of FIG. 1.

FIG. 3 is a diagrammatic view, illustrating use of a device of this invention in measuring the temperature of portions of a person's shoulder.

FIG. 4 is a view taken substantially on line 4—4 of FIG. 3.

DETAILED DESCRIPTION OF THE INVENTION

A temperature sensing device 16 of this invention comprises an opaque flexible elastic membrane 20, which is preferably of a material such as polyurethane or the like, having a thickness preferably of about 0.025 to 0.1 millimeters. The membrane 20 has a coating 24 of temperature-sensing light-reflecting liquid crystals of the type disclosed and described above. The liquid crystals may be encapsulated or non-encapsulated. The coating 24 may be directly applied to the membrane 20 or may be carried by a film which is attached to the membrane 20. The coating 24 preferably has a thickness of about 0.05 to 0.15 millimeters. The peripheral edges of the membrane 20 are shown attached by means of a frame 29 to a rigid or semi-rigid sheet 28 of transparent material, such as LUCITE, and LEXAN or glass. The membrane 20 is attached to the transparent sheet 28 so as to provide a cavity therebetween. The transparent sheet 28 is preferably about 0.1 to 7 millimeters in thickness. However, the sheet 28 may be considerably thicker, depending upon the material of which the sheet 28 is composed and the application of the device.

Within the cavity between the membrane 20 and the sheet 28 is a transparent fill material 30. Preferably, the transparent fill material 30 is one which has a refractive index at twenty-five degrees centigrade (25° C.) greater than one. A suitable fill material 30 may be, for example, mineral oil, water, coconut oil, palm oil, castor oil, water based gel such as 1% ethylene maleic anhydride or silicone gel. A very satisfactory fill material 30 is silicone gel Q3-6527, parts A and B (Dow Corning Corporation, Midland, Michigan) or a silicone gel compound No. RTV6159, parts A and B, sold by General Electric Company. The silicone gel of Dow Corning Corporation, parts A and B, may be from 30% to 70% part A, with the remainder consisting of part B.

The transparent material 30 preferably has limited compressibility and has a degree of elasticity. The transparent material 30 has the ability to transmit light therethrough. The insulator qualities, heat capacity and thermal conductivity of the fill material 30 are such that the thermal contrast and resolution of the thermal image of the coating 24 is enhanced above that which is possible with air or other gas in the cavity between the sheet 28 and the membrane 20. The cavity between the sheet 28 and membrane 20 is free from air or bubbles or other light distortive inclusions. The volume of transparent material 30 within the cavity between the sheet 28 and the membrane 20 may be sufficient to stretch the membrane 20 toward its elastic limit.

In use, the temperature sensing device 16 of this invention is positioned against a surface which may be a non-planar surface, such as a shoulder portion 40 of a person, as illustrated in FIG. 3. The temperature sensing device 16 is held against the shoulder portion 40 by any suitable means, such as manually or by a holder structure or the like, not shown. The membrane 20 engages the shoulder 40 and assumes the shape or contour of the shoulder 40. The heat emitted by the shoulder 40 is transmitted through the membrane 20 to the coating 24 of the microencapsulated liquid crystals. The liquid crystal composition of the coating 24 is one which is selected to be light responsive to the temperature of the shoulder 40. The color reflected by each portion of the coating is dependent upon the temperature thereof. Therefore, the coating 24 provides a thermal image of the shoulder 40. Any abnormalities, such as differing vascular conditions in the shoulder, appear as areas or regions having temperatures different from the temperatures of the other areas or regions of the shoulder. A thermal image 44 may appear somewhat as illustrated in FIG. 4, in which regions 44a and 44b appear in two different colors to indicate two different temperature regions in the shoulder.

The light energy reflected or scattered from the coating 24 is transmitted through the transparent fill material 30 to the sheet 28. The thermal image 44 on the coating 24 is observable through the sheet 28 and the fill material 30. The thermal image 44 on the coating 24 may be recorded by photography or by other means, such as by means of a camera or an electronic device 50 or the like, illustrated in FIG. 3.

The flexible membrane 20 of a device of this invention may be placed in firm contact with any planar or non-planar surface. The non-planar surface may have convex and/or concave portions or may be any configuration or shape. The flexibility of the membrane 20 permits firm contact with any surface engaged thereby. Thus, an excellent thermal image of the surface engaged by the membrane 20 is sensed by the coating 24.

Thus, a device of this invention may be used in numerous medical or veterinarial applications, and may also be used in many other applications. For example, a device of this invention may be employed in industry to obtain thermal images of planar or non-planar surfaces of fabricated or machined parts to define their physical integrity as determined by their thermal image as heat is applied thereto.

Although the preferred embodiment of the microencapsulated cholesteric liquid crystal temperature measuring device of this invention has been described, it will be understood that within the purview of this invention various changes may be made in the form, details, proportion and arrangement of parts, the combination thereof, and the mode of use, which generally stated consists in a structure within the scope of the appended claims.

The invention having thus been described, the following is claimed:

1. A temperature measuring device for measuring the temperature of a surface comprising: a flexible sheet, a coating of microencapsulated cholesteric liquid crystal material covering at least a portion of the flexible sheet, a transparent sheet, means attaching the rigid transparent sheet to the flexible sheet to form a cavity therebetween, a transparent fill material filling the cavity between the flexible sheet and the transparent sheet, the transparent fill material being one in which adjacent portions thereof are relatively movable, the flexible sheet being engageable with a surface and conformable to the contour of the surface for transmission of thermal energy from the surface to the coating, each portion of the coating reflecting light energy in accordance with the temperature thereof and thus providing a thermal image of the surface, the thermal image being observable through the transparent sheet and through the transparent fill material, the composition of the coating comprising:
(a) a polymeric, film-forming binder material and
(b) microcapsules having transparent wall material, and having core material consisting essentially of about 55 to about 75% of cholesteryl pelargonate, about 14 to about 35% of oleyl cholesteryl carbonate, about 2.0 to about 6.0% of cholesteryl propionate and about 4.5 to about 7.2% of cholesteryl chloride.

2. The temperature measuring device of claim 1 wherein the microcapsules are single-droplet microcapsules of uniform size.

3. The temperature measuring device of claim 2 in which the microcapsules are 30 to 50 microns in average diameter.

4. The temperature measuring device of claim 1 wherein the core material consists essentially of about 65–75% cholesteryl pelargonate, about 14–22% oleyl cholesteryl carbonate, about 4.5–6.0% cholesteryl propionate and about 6.2–7.2% cholesteryl chloride.

5. The temperature measuring device of claim 4 in which the composition of the coating comprises about equal parts of two kinds of microcapsules, differing in core material compositions, wherein the first kind of microcapsule has core material about 2.4 to about 4.7% richer in cholesteryl pelargonate and about 3.3 to about 4.7 poorer in oleyl cholesteryl carbonate than the core material of the second kind of microcapsule.

6. The temperature measuring device of claim 4 wherein the selected microcapsule core material composition is one or two of the following:

| % Cholesteryl Pelargonate | % Oleyl Cholesteryl Carbonate | % Cholesteryl Propionate | % Cholesteryl Chloride |
|---|---|---|---|
| (a) 66.4 | 21.6 | 5.5 | 6.5 |
| (b) 66.5 | 22.0 | 4.6 | 6.9 |
| (c) 68.0 | 20.3 | 4.7 | 7.0 |
| (d) 70.0 | 18.3 | 4.7 | 7.0 |
| (e) 71.0 | 17.3 | 4.7 | 7.0 |
| (f) 72.7 | 15.6 | 4.7 | 7.0 |
| (g) 73.2 | 15.0 | 5.4 | 6.4 |
| (h) 73.4 | 14.5 | 5.6 | 6.5 |

7. The temperature measuring device of claim 6 wherein selected microcapsule core material is one of compositions (b), (c), (d), (e), and (f).

8. The temperature measuring device of claim 6 wherein two microcapsule core materials are used in about equal portions, selected as follows: (a) and (d), (b) and (e), (c) and (f), (d) and (g) or (e) and (h).

9. The temperature measuring device of claim 6 wherein two microcapsule core materials are used in unequal portions, up to a 70-30 ratio selected as follows: (a) and (d), (b) and (e), (c) and (f), (d) and (g) or (e) and (h).

10. The temperature measuring device of claim 1 wherein the core material consists essentially of about 55-67% cholesteryl pelargonate, about 25-35% oleyl cholesteryl carbonate, about 2.0-4.1 cholesteryl propionate and about 4.5 to 5.6 cholesteryl chloride.

11. The temperature measuring device of claim 10 in which the composition of the coating comprises about equal parts of two kinds of microcapsules, different in core material compositions, wherein the first kind of microcapsule has core material about 1.5 to about 3.1% richer in cholesteryl pelargonate and about 0.8 to about 3.5% poorer in oleyl cholesteryl carbonate than the core material of the second kind of microcapsule.

12. The temperature measuring device of claim 11 wherein the selected microcapsule core material is one or two of the following:

| % Cholesteryl Pelargonate | % Oleyl Cholesteryl Carbonate | % Cholesteryl Propionate | % Cholesteryl Chloride |
|---|---|---|---|
| (a) 58.6 | 31.7 | 4.1 | 5.6 |
| (b) 61.1 | 29.6 | 3.7 | 5.6 |
| (c) 63.0 | 28.4 | 3.0 | 5.6 |
| (d) 58.5 | 33.9 | 2.4 | 5.2 |
| (e) 60.7 | 31.5 | 2.4 | 5.4 |
| (f) 61.2 | 31.5 | 2.5 | 4.8 |
| (g) 62.2 | 30.7 | 2.1 | 5.0 |
| (h) 63.5 | 29.2 | 2.2 | 5.1 |
| (i) 65.3 | 27.2 | 2.6 | 4.9 |
| (j) 66.3 | 26.2 | 2.6 | 4.9 |

13. The temperature measuring device of claim 12 wherein two microcapsule core materials are used in about equal portions, selected as follows: (a) and (b), (b) and (c), (c) and (e), (d) and (f), (e) and (g), (f) and (h), (g) and (i) or (h) and (j).

14. The temperature measuring device of claim 12 measuring two microcapsule core materials are used in unequal portions, up to a 70-30 ratio, selected as follows: (a) and (b), (b) and (c), (c) and (e), (d) and (f), (e) and (g), (f) and (h), (g) and (i) or (h) and (j).

15. The temperature measuring device of claim 1 in which the wall material is gelatin.

16. The temperature measuring device of claim 1 in which the wall material is melamine formaldehyde resin.

17. The temperature measuring device of claim 1 wherein the binder material is polyurethane and the microcapsule wall material is urea-formaldehyde resin.

* * * * *

UNITED STATES PATENT AND TRADEMARK OFFICE
CERTIFICATE OF CORRECTION

PATENT NO. : 4,433,637
DATED : February 28, 1984
INVENTOR(S) : William L. Buirley, Donald E. Koopman,
David B. McQuain and William H. Reeves It is certified that error appears in the above-identified patent and that said Letters Patent are hereby corrected as shown below:

Column 5, line 3, change "and" to ---or---.

Claim 14, Column 8, line 30, change "measuring" to

---wherein---.

Signed and Sealed this

Twenty-sixth Day of June 1984

[SEAL]

*Attest:*

*Attesting Officer*

GERALD J. MOSSINGHOFF

*Commissioner of Patents and Trademarks*